(12) United States Patent
Watanabe et al.

(10) Patent No.: US 7,691,586 B2
(45) Date of Patent: Apr. 6, 2010

(54) METHOD FOR PREDICTING AND JUDGING THE RECURRENCE OF LIVER CANCER AFTER TREATING LIVER CANCER

(75) Inventors: Kiyotaka Watanabe, Bunkyo-ku (JP); Shin Ohnishi, Bunkyo-ku (JP); Hiroyuki Aburatani, Musashino (JP); Yutaka Midorikawa, Shinagawa-ku (JP); Yoshitaka Hippo, Komae (JP); Hiroko Iwanari, Meguro-ku (JP); Susumu Tokita, Nishinomiya (JP); Hirokazu Satoh, Meguro-ku (JP)

(73) Assignee: Perseus Proteomics Inc., Tokyo (JP)

( * ) Notice: Subject to any disclaimer, the term of this patent is extended or adjusted under 35 U.S.C. 154(b) by 342 days.

(21) Appl. No.: 11/587,995

(22) PCT Filed: Apr. 28, 2005

(86) PCT No.: PCT/JP2005/008194

§ 371 (c)(1),
(2), (4) Date: Oct. 30, 2006

(87) PCT Pub. No.: WO2005/106485

PCT Pub. Date: Nov. 10, 2005

(65) Prior Publication Data

US 2008/0138827 A1 Jun. 12, 2008

(30) Foreign Application Priority Data

Apr. 28, 2004 (JP) ............................. 2004-134008
Sep. 24, 2004 (JP) ............................. 2004-276704

(51) Int. Cl.
*G01N 33/53* (2006.01)
*G01N 33/567* (2006.01)
*G01N 33/574* (2006.01)
*C07K 16/00* (2006.01)

(52) U.S. Cl. ................. 435/7.1; 435/7.21; 435/7.23; 530/387.1; 530/387.7

(58) Field of Classification Search ................. None
See application file for complete search history.

(56) References Cited

U.S. PATENT DOCUMENTS

2003/0219767 A1* 11/2003 Ayers et al. ............... 435/6

FOREIGN PATENT DOCUMENTS

| EP | 1 541 680 A1 | 6/2005 |
| WO | WO 03/100429 A2 | 12/2003 |
| WO | WO 2004/018667 A1 | 3/2004 |
| WO | WO 2004/022597 A1 | 3/2004 |

OTHER PUBLICATIONS

Tockman et al (Cancer Res., 1992, 52:2711s-2718s).*
Capurro et al. (Gastroenterology, Jul. 2003 125:89-97).*
Freshney (Culture of Animal Cells, A Manual of Basic Technique, Alan R. Liss, Inc., 1983, New York, p. 3-4).*
Dermer (Bio/Technology, 1994, 12:320).*
Mast et al. (Biochemical J. 1997, 327: 577-583).*
Trojan et al. (Digestion 1998; 59(suppl. 2): 72-74).*
Koh et al. (Hepato-Gastroenterology, 2002 49:1615-1618).*
Hippo, et al., "Identification of Soluble NH2-Terminal Fragment of Glypican-3 as a Serological Marker for Early-Stage Hepatocellular Carcinoma", Cancer Research, vol. 64, pp. 2418-2423, 2004.
Tetsuya Nakatsura, et al., "Glypican-3, overexpressed specifically in human hepatocellular carcinoma, is a novel tumor marker", Biochemical and Biophysical Research, XP002261242, vol. 306, Jun. 19, 2003, pp. 16-25.
Yoshitaka Fukuzawa, et al., "Expression of glypican-3 (GPC 3) and its significance as a novel marker of the degree of dedifferentiation in hepatocellular carcinoma (HCC)", Hepatology, XP008081663, vol. 36, No. 4 part 2, 2002, p. 691A.

* cited by examiner

*Primary Examiner*—Peter J Reddig
(74) *Attorney, Agent, or Firm*—Oblon, Spivak, McClelland, Maier & Neustadt, L.L.P.

(57) ABSTRACT

A method for prognosing possible recurrence after treatment of the liver cancer, characterized by measuring GPC3 contained in a test sample by use of an anti-GPC3 antibody.

14 Claims, 1 Drawing Sheet

Fig. 1

METHOD FOR PREDICTING AND JUDGING THE RECURRENCE OF LIVER CANCER AFTER TREATING LIVER CANCER

TECHNICAL FIELD

The present invention relates to a method of prognosing the recurrence after treating liver cancer, and to a agent for said prognosis.

BACKGROUND ART

Primary hepatocellular carcinoma (hereinafter may be referred to as "liver cancer") most often appears after progression of chronic hepatitis to cirrhosis. Many viral hepatitis and cirrhosis patients have been recognized, and, in recent years, incidence of liver cancer has been increasing. Liver cancer has been treated with, for example, hepatectomy, percutaneous local therapy (e.g., radiofrequency ablation therapy or ethanol injection therapy), transcatheter hepatic arterial embolization (TAE), continuous arterial infusion chemotherapy, or radiation therapy.

Liver cancer therapy is selected in consideration of the distribution and size of cancerous cells, and as well the underlying hepatic disorder (hepatitis or cirrhosis). Even when liver cancer patients are treated with a highly radical therapy, incidence of post-treatment intrahepatic ectopic recurrence is as high as 10 to 30% per year. Such post-treatment recurrence leads to poor prognosis of cancer-bearing patients. In consideration of such a high ectopic recurrence rate, patients who have undergone liver cancer treatment are followed up with frequent imaging or tests employing tumor markers.

Tumor markers which have conventionally been employed for liver cancer diagnosis include α-fetoprotein (AFP), α-fetoprotein lectin fraction (L3 fraction), and PIVKA-II. Such a tumor marker is fairly useful for liver cancer diagnosis, evaluation of therapeutic effect, and diagnosis of post-treatment recurrence in a high-risk patient with, for example, viral hepatitis or cirrhosis, but the tumor marker is often false-positive or false-negative. Therefore, clinically, diagnosis employing such a tumor marker is performed in combination with another imaging technique (e.g., abdominal ultrasound examination or CT scan), or through periodical analysis. A tumor marker which can evaluate the risk of liver cancer recurrence in background liver tissue immediately after treatment could provide advantages in that, for example, recurrence of liver cancer can be detected early, a more radical therapy causing no impairment of background liver disorder can be carried out, and load due to frequent examination can be reduced in patients with low recurrence risk. Therefore, demand has arisen for a diagnostic marker which is useful for prognosing the posttreatment recurrence of liver cancer.

A glypican family has been reported to be present, as a new family of heparan sulfate proteoglycan, on the surfaces of cells. As has been reported so far, the glypican family includes six glypican members (glypican-1, glypican-2, glypican-3, glypican-4, glypican-5, and glypican-6). The glypican family members have a core protein of uniform size (about 60 kDa), share a specific and well-retained cysteine arrangement, and are bound to the cell membrane by means of a glycosylphosphatidylinositol (GPI) anchor.

Glypican-3 (GPC3) has been known to be closely related to developmental cell division or control of cell division patterns. As has also been known, the GPC3 gene is highly expressed in liver cancer cells, and may be suitable for employment as a hepatocellular carcinoma marker. In addition, Patent Documents 1 and 2 have already disclosed a method for diagnosing cancer through measurement of GPC3. However, the manner in which GPC3 level changes after liver cancer treatment has never been known, nor has establishment of a therapeutic strategy through analysis of change in GPC3 level.

Patent Document 1: International Publication WO 03/100429 pamphlet

Patent Document 2: International Publication WO 2004/018667 pamphlet

DISCLOSURE OF THE INVENTION

Problems to be Solved by the Invention

In view of the foregoing, an object of the present invention is to provide means for prognosing posttreatment recurrence of liver cancer, which has conventionally been difficult to predict.

Means for Solving the Problems

The present inventors have measured the level of GPC3 in the body fluids of patients before and after liver cancer treatment, and have conducted long-term follow-up studies on the relation between the thus-measured GPC3 level and recurrence of liver cancer. As a result, the present inventors have found that blood GPC3 is useful as a factor for prognosing recurrence of liver cancer, despite a failure of a common tumor marker (i.e., AFP, AFP-L3 fraction, or PIVKA-II) to exhibit sufficient correlation with liver cancer recurrence. The present invention has been accomplished on the basis of this finding.

Accordingly, the present invention provides an agent for prognosing a posttreatment recurrence of liver cancer containing an anti-GPC3 antibody.

The present invention also provides a method of prognosing posttreatment recurrence of liver cancer, characterized by measuring GPC3 contained in a test sample by use of an anti-GPC3 antibody.

EFFECTS OF THE INVENTION

The present invention enables prediction of post-treatment recurrence of liver cancer, which prediction is difficult by a conventional tumor marker, and as well design of a new therapeutic regimen.

BEST MODE FOR CARRYING OUR THE INVENTION

The present invention will next be described in detail.

The present invention provides a method of prognosing posttreatment recurrence of liver cancer through measurement of GPC3 contained in a test sample by use of an anti-GPC3 antibody.

As used herein, the term "measurement" refers to quantitative determination or non-quantitative determination. Examples of non-quantitative determination include determining simply whether or not GPC3 is present, determining whether or not GPC3 is present in a predetermined amount or more, and comparing the amount of GPC3 contained in a test sample with that of GPC3 contained in another sample (e.g., a control sample). Examples of quantitative determination include measurement of the level of GPC3, and measurement of the amount of GPC3.

No particular limitation is imposed on the test sample to be employed, so long as the sample possibly contains GPC3. However, the test sample is preferably a sample collected from a living body such as a mammal, more preferably a sample collected from a human. Specific examples of the test sample include blood, interstitial fluid, plasma, extravascular fluid, cerebrospinal fluid, synovial fluid, pleural fluid, serum, lymph, saliva, and urine. Of these, blood, serum, and plasma are preferred. In the present invention, the test sample encompasses a sample prepared from a test sample, such as a culture medium of cells collected from a living body.

The test sample employed in the present invention is particularly preferably blood, serum, or plasma collected from a patient who has undergone liver cancer treatment. The patient who has undergone liver cancer treatment may be a patient who has undergone hepatectomy, radiofrequency ablation therapy, ethanol injection therapy, TAE, continuous arterial infusion chemotherapy, or a similar therapy, but is particularly preferably a patient who has undergone a highly radical therapy (i.e., hepatectomy, radiofrequency ablation therapy, or ethanol injection therapy).

The anti-GPC3 antibody employed in the present invention may be a monoclonal antibody or a polyclonal antibody, but particularly preferably is a monoclonal antibody. The anti-GPC3 antibody is preferably an antibody against secretory GPC3 (i.e., an anti-soluble-GPC3 antibody), in view that blood, serum, or plasma is employed as a test sample. The anti-GPC3 antibody to be employed is particularly preferably an anti-soluble-GPC3 monoclonal antibody. Next will be described in detail the case where an anti-GPC3 monoclonal antibody is employed.

1. Preparation of Anti-GPC3 Monoclonal Antibody.

No particular limitation is imposed on the origin and form of the anti-GPC3 monoclonal antibody employed in the present invention, so long as the antibody binds specifically to GPC3 protein. Specific examples of the anti-GPC3 monoclonal antibody which may be employed include known monoclonal antibodies such as mouse antibody, rat antibody, human antibody, chimeric antibody, and humanized antibody. Preferably, an anti-GPC3 monoclonal antibody immobilized on a support recognizes an epitope of GPC3 molecule which differs from that is recognized by an anti-GPC3 monoclonal antibody labeled with a labeling substance. No particular limitation is imposed on the site of such an epitope.

The anti-GPC3 monoclonal antibody employed in the present invention can be prepared through a known technique. The anti-GPC3 monoclonal antibody employed in the present invention is particularly preferably a monoclonal antibody derived from a mammal. The mammal-derived monoclonal antibody includes a monoclonal antibody produced in a hybridoma, and a monoclonal antibody produced in a host transformed with an expression vector containing a gene for the antibody through a genetic engineering technique.

A hybridoma which produces the monoclonal antibody can be basically prepared as described below through a known technique. Specifically, the hybridoma can be prepared through the following procedure: a mammal is immunized with GPC3, soluble GPC3, or a peptide fraction thereof, which serves as an immunogen, through a customary immunization method; the resultant immunocyte is fused with a known parental cell through a customary cell fusion method; and a cell for producing the monoclonal antibody is selected through a customary screening method.

Specifically, the monoclonal antibody can be prepared as follows.

Firstly, GPC3, which is employed as an immunogen for preparing the monoclonal antibody, can be obtained through purification of natural GPC3 contained in a culture supernatant prepared through culturing of, for example, HuH6 or HepG2 cell line. Alternatively, GPC3 can be obtained through expression of GPC3 (MXR7) gene/amino acid sequence disclosed in Lage, H., et al., Gene 188 (1997), 151-156. Specifically, an appropriate host cell is transformed with a known expression vector containing the gene sequence encoding GPC3, and then a target human GPC3 protein is purified from the resultant host cell or a culture supernatant of the cell through a known method.

Subsequently, the thus-purified GPC3 is employed as an immunogen. The immunogen may be a partial peptide of GPC3. Such a GPC3 partial peptide may be, obtained through chemical synthesis on the basis of the amino acid sequence of human GPC3, through integration of a portion of the GPC gene into an expression vector, or through degradation of natural GPC3 by means of proteolytic enzyme. No limitation is imposed on the site or size of a GPC3 portion to be employed as a partial peptide. In the present invention, the immunogen to be employed is preferably full-length GPC3.

No particular limitation is imposed on the mammal to be immunized with the immunogen, but preferably, the mammal is selected in consideration of adaptability to parental cells employed in cell fusion. In general, a rodent animal (e.g., mouse, rat, hamster, or guinea pig), rabbit, monkey, chicken, or the like is employed.

Immunization of an animal with the immunogen is performed through a known method. For example, in a generally employed immunization method, the immunogen is intraperitoneally or subcutaneously injected in a mammal. Specifically, the immunogen is diluted and suspended in an appropriate amount of PBS (phosphate-buffered saline), physiological saline, etc., and, if desired, the resultant suspension is mixed with an appropriate amount of a conventional adjuvant (e.g., Freund's complete adjuvant). After the resultant mixture is emulsified, the emulsion is administered to a mammal several times every 4 to 21 days interval. During the course of immunization with the immunogen, an appropriate carrier may be employed. Particularly when the immunogen is a partial peptide of low molecular weight, preferably, the partial peptide employed for immunization is bound to a carrier protein such as albumin or keyhole limpet hemocyanin.

After a mammal is immunized as described above, and then an increase in the level of a target antibody in serum is observed, an immunocyte is collected from the mammal, and then subjected to cell fusion. The immunocyte is particularly preferably splenocyte.

A mammalian myeloma cell is employed as the parental cell to be fused with the aforementioned immunocyte. The myeloma cells to be employed are preferably a known cell strains; for example, P3 (P3X63Ag8.653) (J. Immnol. (1979) 123, 1548-1550), P3X63Ag8U.1 (Current Topics in Microbiology and Immunology (1978) 81, 1-7), NS-1 (Kohler. G. and Milstein, C. Eur. J. Immunol. (1976) 6, 511-519), MPC- 11 (Margulies. D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), S194 (Trowbridge, I. S. J. Exp. Med. (1978) 148, 313-323), or R210 (Galfre, G. et al., Nature (1979) 277, 131-133).

Cell fusion between the aforementioned immunocyte and myeloma cell can be basically performed through a known method, such as the method of Kohler, Milstein, et al. (Kohler. G. and Milstein, C., Methods Enzymol. (1981) 73, 3-46).

More specifically, the cell fusion is performed in a conventional nutritive culture medium in the presence of, for example, a cell fusion accelerator. Examples of the cell fusion accelerator to be employed include polyethylene glycol (PEG) and Sendai virus (HVJ). If desired, an auxiliary agent (e.g., dimethyl sulfoxide) may be further added in order to enhance cell fusion efficiency.

The ratio of the immunocyte to myeloma cell may be predetermined arbitrarily. For example, the number of the immunocyte is preferably larger 1 to 10 times that of the myeloma cell. Examples of the culture medium which may be employed for the aforementioned cell fusion include RPMI1640 medium and MEM medium, which are suitable for proliferation of the aforementioned myeloma cell line; and media which are generally employed for culturing of such a cell. Such a culture medium may be employed in combination with a serum supplement such as fetal calf serum (FCS).

In the cell fusion, predetermined amounts of the aforementioned immunocyte and myeloma cell are well-mixed in any of the aforementioned culture media, and a solution of PEG (e.g., PEG having an average molecular weight of about 1,000 to about 6,000) which has been heated in advance to about 37° C. is added to the resultant mixture in a predetermined amount (generally 30 to 60% (w/v)), followed by mixing, to thereby form a target hybridoma. Subsequently, a procedure (including sequential addition of an appropriate culture medium, and removal of a supernatant obtained through centrifugation) is repeated, to thereby remove substances (e.g., cell fusion promoting reagent) which are not suitable for growth of the hybridoma.

Separation of the thus-formed hybridoma is performed through culturing in a conventional selective culture medium such as HAT medium (medium containing hypoxanthine, aminopterin, and thymidine). Culturing in the aforementioned HAT medium is continued for a sufficient period of time (generally several days to several weeks) to kill cells (i.e., non-fused cells) other than a target hybridoma. Subsequently, a conventional limiting dilution technique is performed for screening and monocloning of the hybridoma which produces a target antibody.

Screening and monocloning of a target antibody can be performed through a screening method on the basis of known antigen-antibody reaction. For example, an antigen is bound to a solid support (e.g., beads formed of polystyrene or a similar material, or a commercially available 96-well microtiter plate) and then reacted with a culture supernatant of the hybridoma, and subsequently the support is washed, followed by reaction with, for example, an enzyme-labeled secondary antibody, to thereby determine whether or not the culture supernatant contains a target antibody which reacts with a immunogen. Cloning of the hybridoma which produces a target antibody can be performed through, for example, a limiting dilution technique. In this case, the antigen may be the same antigen as employed in immunization.

In addition to preparation of the aforementioned hybridoma through immunization of an animal (other than human) with an antigen, a desired human antibody having binding activity to GPC3 can be obtained by sensitizing human lymphocyte with GPC3 in vitro, and fusing the thus-sensitized lymphocyte with a human-derived myeloma cell having unlimited division capacity (see Japanese Patent Publication (kokoku) No. 1-59878). Alternatively, GPC3 serving as an antigen may be administered to a transgenic animal having all the human antibody gene repertoires, to thereby yield a cell which produces an anti-GPC3 monoclonal antibody, and a human antibody against GPC3 may be obtained from the cell after it has been immortalized (see WO 94/25585, WO 93/12227, WO 92/03918, and WO 94/02602).

The thus-formed monoclonal-antibody-producing hybridoma can be subcultured in a conventional culture medium, and can be stored in liquid nitrogen for a long period of time.

A monoclonal antibody is obtained from the hybridoma through, for example, a method in which the hybridoma is cultured with a conventional technique, and the monoclonal antibody is obtained from the resultant culture supernatant; or a method in which the hybridoma is administered to a mammal adaptable to the hybridoma and proliferated in the body, and resultant the monoclonal antibody is obtained from ascites of the mammal. The former method is suitable for obtaining a monoclonal antibody of high purity, whereas the latter method is suitable for mass production of a monoclonal antibody.

The monoclonal antibody employed in the present invention may be a recombinant antibody. Such a recombinant antibody is produced through the following procedure: the antibody gene is cloned from the hybridoma; the gene is integrated into an appropriate vector; and the vector is introduced into a host, followed by production of the recombinant antibody through a genetic recombination technique (see, for example, Vandamme, A. M., et al., Eur. J. Biochem. (1990) 192, 767-775, 1990). Specifically, mRNA encoding a variable (V) region of an anti-GPC3 monoclonal antibody is isolated from the hybridoma which produces the anti-GPC3 monoclonal antibody. Isolation of mRNA is performed as follows. Total RNA is prepared through a known method such as the guanidine ultracentrifugation method (Chirgwin, J. M., et al., Biochemistry (1979) 18, 5294-5299) or the AGPC method (Chomczynski, P., et al., Anal. Biochem. (1987) 162, 156-159), and target mRNA is prepared by means of, for example, an mRNA Purification Kit (product of Pharmacia). Alternatively, mRNA may be directly prepared by means of QuickPrep mRNA Purification Kit (product of Pharmacia).

The thus-obtained mRNA is employed for synthesis of cDNA of the antibody variable (V) region by use of reverse transpriptase. Synthesis of cDNA is performed by means of, for example, AMV Reverse Transcriptase First-strand cDNA Synthesis Kit (product of Seikagaku Corporation). Alternatively, synthesis and amplification of cDNA may be performed by means of, for example, 5'-Ampli FINDER RACE Kit (product of Clontech) and the 5'-RACE method (Frohman, M. A., et al., Proc. Natl. Acad. Sci. USA (1988) 85, 8998-9002, Belyavsky, A., et al., Nucleic Acids Res. (1989) 17, 2919-2932) employing PCR.

A target DNA fragment is purified from the resultant PCR product, and ligated to vector DNA. Subsequently, a recombinant vector is prepared from the vector DNA, and then introduced into *Escherichia coli* or the like, followed by colony selection, to thereby prepare a desired recombinant vector. The nucleotide sequence of target DNA is verified through a known method such as the dideoxynucleotide chain termination method.

After DNA encoding the V regions of a target anti-GPC3 monoclonal antibody is obtained, the DNA is integrated into an expression vector containing DNA encoding the constant (C) regions of the target antibody.

In order to produce the anti-GPC3 monoclonal antibody employed in the present invention, the gene for the antibody is integrated into an expression vector in such a manner that the gene can be expressed under control of an expression regulatory region such as an enhancer or a promoter. Subsequently, a host cell is transformed with this expression vector for expression of the antibody.

The gene for the antibody may be expressed by simultaneously transforming a host cell with an expression vector containing the DNA encoding the heavy chain (H chain) of the antibody and an expression vector containing the DNA encoding the light chain (L chain) of the antibody, or by transforming a host cell with a single expression vector containing the DNA encoding the heavy and light chains of the antibody (see WO 94/11523).

In addition to the aforementioned host cell, a transgenic animal can be employed for production of recombinant antibodies. For example, an antibody gene is inserted into a gene encoding a protein produced specifically in milk (such as goat β casein) to prepare a fusion gene. A DNA fragment including the fusion gene having the inserted antibody gene is injected into the embryo of a goat, and this embryo is implanted into a female goat. A desired antibody is obtained from the milk produced by transgenic goats born from the goat impregnated with the embryo or progeny thereof. In order to increase the amount of the antibody-containing milk produced by the transgenic goats, hormones may be administered to the transgenic goats as appropriate (Ebert, K. M. et al., Bio/Technology (1994) 12, 699-702).

In the present invention, in addition to the aforementioned antibodies, an artificially modified, genetically recombinant antibody (e.g., a chimeric antibody or a humanized antibody) can be employed. Such a modified antibody can be produced through a known method.

Specifically, a chimeric antibody is prepared through the following procedure: the above-obtained DNA encoding the antibody V regions is ligated to the DNA encoding the human antibody C regions; the thus-ligated DNA is integrated into an expression vector; and the expression vector is introduced into a host for production of the chimeric antibody. Through this known procedure, a chimeric antibody useful for the present invention can be prepared.

A humanized antibody is also called a "reshaped human antibody," and is obtained by grafting the complementarity determining regions (CDRs) of an antibody from a non-human mammal (e.g., mouse) into the CDRs of a human antibody. Typical gene recombination techniques for preparing such a humanized antibody are known (see EP 125023 and WO 96/02576).

Specifically, a DNA sequence designed to ligate the CDRs of a mouse antibody to the framework regions (FRs) of a human antibody is synthesized through PCR employing, as primers, several oligonucleotides prepared to have portions overlapping terminal regions of both the CDRs and FRs (see the method described in WO 98/13388).

The FRs of the human antibody ligated via the CDRs are selected in such a manner that the CDRs form a proper antigen-binding site. If necessary, amino acids in the FRs of the antibody variable regions may be substituted so that the CDRs of a reshaped humanized antibody form a proper antigen-binding site (Sato, K., et al., Cancer Res. (1993) 53, 851-856).

The C regions employed in a chimeric antibody or a humanized antibody may be those of a human antibody; for example, Cγ1, Cγ2, Cγ3, and Cγ4 in the H chain, and Cκ and Cλ in the L chain. The C regions of the human antibody may be modified so as to improve the stability of the antibody or production thereof.

The chimeric antibody consists of the V regions of an antibody derived from a non-human mammal and the C regions of a human antibody. Meanwhile, the humanized antibody consists of the CDRs of an antibody derived from a non-human mammal, whereas the FRs and C regions of a human antibody.

The antibody employed in the present invention is not limited to whole molecule antibodies. So long as the antibody binds to GPC3, the antibody may be an antibody fragment, a modified antibody fragment, a divalent antibody, or a monovalent antibody. Examples of the antibody fragment include Fab, (Fab')2, Fv, Fab/c having one Fab and complete Fc, and single-chain Fv (scFv) in which Fv fragments of the H or L chain are linked together with an appropriate linker. Specifically, an antibody is treated with an enzyme (e.g., papain or pepsin) to produce antibody fragments. Alternatively, the genes encoding these antibody fragments are formed, and introduced into an expression vector, followed by expression in an appropriate host cell (see, for example, Co, M. S., et al., J. Immunol. (1994) 152, 2968-2976, Better, M. & Horwitz, A. H. Methods in Enzymology (1989) 178, 476-496, Academic Press, Inc., Plueckthun, A. & Skerra, A. Methods in Enzymology (1989) 178, 476-496, Academic Press, Inc., Lamoyi, E., Methods in Enzymology (1989) 121, 652-663, Rousseaux, J., et al., Methods in Enzymology (1989) 121, 663-669, and Bird, R. E., et al., TIBTECH (1991) 9, 132-137).

The fragment scFv is obtained by linking the H chain V region and L chain V region of an antibody. In the scFv fragment, the H chain V region and the L chain V region are linked by means of a linker (preferably, a peptide linker) (Huston, J. S., et al., Proc. Natl. Acad. Sci. U.S.A. (1988) 85, 5879-5883). The H chain V region and the L chain V region in the scFv fragment may be derived from any of the antibodies described herein. The peptide linker to be employed for linking the V regions is, for example, any single-stranded peptide consisting of 12 to 19 amino acid residues.

DNA encoding the scFv fragment is obtained through PCR amplification employing, as a template, the entire sequence of the DNA encoding the H chain or H chain V region of the aforementioned antibody or the DNA encoding the L chain or L chain V region of the antibody, or a portion of the DNA sequence encoding a desired amino acid sequence, in combination with primer pairs defining both ends of the DNA sequence, followed by amplification employing the DNA encoding a peptide linker region in combination with a primer pair which defines both ends of the DNA so that the respective ends are linked to the H and L chains.

Once the DNA encoding the scFv fragment is prepared, an expression vector containing the DNA and a host transformed with the expression vector can be obtained through a customary method, and the scFv fragment can be obtained through a standard method by use of the host.

Such an antibody fragment can be produced by a host after obtaining and expressing the gene for the fragment in a manner similar to that described above. As used herein, the term "antibody" also encompasses such an antibody fragment.

As a modified product of an antibody, an anti-GPC3 antibody, which is bound to one of various molecules such as a labeling substance, may also be employed. As used herein, the term "antibody" also encompasses such a modified antibody. Such a modified antibody can be obtained through chemical modification of the above-obtained antibody. Methods for modifying antibodies have already been established in the art.

Also, the antibody employed in the present invention may be a bispecific antibody. The bispecific antibody may have antigen-binding sites recognizing different epitopes of GPC3 molecule, or may have an antigen-binding site recognizing GPC3 and an antigen-binding site recognizing a labeling substance or the like. A bispecific antibody can be prepared by binding HL pairs of two antibodies, or obtained from a bispecific-antibody-producing fused cell prepared through fusion of hybridomas producing different monoclonal antibodies. A bispecific antibody can also be prepared through a genetic engineering technique.

The above-formed gene for the antibody can be expressed through a known method, to thereby yield the antibody. In the case where a mammalian cell is employed, the antibody gene can be expressed by operably ligating a useful conventional promoter, the gene to be expressed, and polyA signal downstream of the 3' end thereof. Examples of the promoter/enhancer which may be employed include human cytomegalovirus immediate early promoter/enhancer.

Other promoters/enhancers which can be employed for antibody expression in the present invention include viral promoters/enhancers such as retrovirus, polyomavirus, adenovirus, and simian virus 40 (SV40); and promoters/enhancers derived from mammalian cells, such as human elongation factor 1a (HEF1a).

When SV40 promoter/enhancer is employed, gene expression can be readily performed through the method of Mulligan, et al. (Nature (1979) 277, 108), whereas when HEF1a promoter/enhancer is employed, gene expression can be readily performed through the method of Mizushima, et al. (Nucleic Acids Res. (1990) 18, 5322).

In the case where *Escherichia coli* is employed, the gene for the antibody can be expressed by operably ligating useful promoter with a signal sequence for secreting the antibody, and the antibody gene to be expressed. Example of the promoter which may be employed includes lacz promoter and araB promoter. When lacz promoter is employed, the gene can be expressed through the method of Ward, et al. (Nature (1098) 341, 544-546; FASEB J. (1992) 6, 2422-2427), whereas when araB promoter is employed, the gene can be expressed through the method of Better, et al. (Science (1988) 240, 1041-1043).

When the antibody is to be produced in the periplasm of *Escherichia coli*, the pelB signal sequence (Lei, S. P., et al., J. Bacteriol. (1987) 169, 4379) may be employed as a signal sequence for secreting the antibody. The antibody produced in the periplasm is isolated, and then employed by appropriately refolding the structure of the antibody.

Replication origins which may be employed include those derived from SV40, polyomavirus, adenovirus, bovine papilloma virus (BPV), etc. In order to amplify gene copy number in a host cell system, an expression vector to be employed may contain a selective marker such as aminoglycoside transferase (APH) gene, thymidine kinase (TK) gene, *Escherichia coli* xanthine-guanine phosphoribosyl transferase (Ecogpt) gene, or dihydrofolate reductase (dhfr) gene.

Any expression systems such as a eukaryotic or prokaryotic system can be used for production of the antibody employed in the present invention. Examples of the eukaryotic cell which may be employed include established cell systems such as a mammalian cell, insect cell line, mycotic cell, and yeast cell; and examples of the prokaryotic cell which may be employed include bacterial cells such as *Escherichia coli* cell.

Preferably, the antibody employed in the present invention is expressed in mammalian cells such as CHO, COS, myeloma, BHK, Vero, or HeLa.

Subsequently, the above-transformed host cells are cultured in vitro or in vivo to produce a target antibody. Culture of the host cell is performed through a known method. For example, DMEM, MEM, PRMI1640, or IMDM can be employed as a culture medium, and a serum supplement such as fetal calf serum (FCS) may be employed in combination.

The above-expressed or produced antibody can be isolated from a cell or host animal and purified to homogeneity. Isolation and purification of the antibody employed in the present invention can be performed by means of an affinity column. Example of protein A column include Hyper D, POROS, and Sepharose F.F. (product of Pharmacia). No particular limitation is imposed on the method for isolation/purification of the antibody, and the antibody can be isolated or purified through any method which is generally employed for isolation/separation of proteins. For example, the antibody can be isolated/purified by appropriately selecting or combining chromatography columns other than the aforementioned affinity columns, filters, ultrafiltration, salting out, dialysis, etc. (Antibodies A Laboratory Manual. Ed Harlow, David Lane, Cold Spring Harbor Laboratory, 1988).

No particular limitation is imposed on the epitope of the antibody employed in the present invention, so long as the antibody recognizes full-length GPC3 or a peptide fraction thereof. More specifically, the present invention can employ a monoclonal antibody or polyclonal antibody produced by the hybridoma described in, for example, WO 03/10049, WO 2004/018667, or PCT/JP2002/008990. Particularly preferably, monoclonal and polyclonal antibodies prepared in Examples 2 and 3 are employed.

2. Measurement of GPC3

In the present invention, GPC3 to be measured may be GPC3 protein to which heparan sulfate or the like is attached, or GPC3 core protein.

GPC3 contained in a test sample is measured through an immunological method employing an anti-GPC3 antibody. Examples of the immunological method include radioimmunoassay, enzyme immunoassay, fluoroimmunoassay, luminescence immunoassay, immunoprecipitation, immunonephelometry, Western blotting, immunostaining, and immunodiffusion. Of these, enzyme immunoassay is preferred, with enzyme-linked immunosorbent assay (ELISA) (e.g., sandwich ELISA) being particularly preferred. Any of the aforementioned immunological methods (e.g., ELISA) can be performed in a manner known to those skilled in the art.

Measurement of GPC3 by use of an anti-GPC3 antibody is generally performed through, for example, the following procedure: an anti-GPC3 antibody is immobilized on a support, and a test sample is added thereto; the anti-GPC3 antibody is bound to GPC3 protein through incubation, followed by washing; and the GPC3 protein which is bound to the support via the anti-GPC3 antibody is measured, to thereby measure the GPC3 protein contained in the test sample.

Examples of the support which may be employed in the present invention include insoluble polysaccharides such as agarose and cellulose; synthetic resins such as silicone resin, polystyrene resin, polyacrylamide resin, nylon resin, and polycarbonate resin; and insoluble supports such as glass. Such a support may be employed in the form of, for example, beads or plate. In the case where the support is in the form of beads, for example, a column filled with support beads may be employed. In the case where the support is in the form of plate, for example, a multi-well plate (e.g., a 96-well plate) or a biosensor chip may be employed. Binding between an anti-GPC3 antibody and a support can be performed through a generally employed technique such as chemical binding or physical adsorption. Any of the aforementioned supports may be a commercially available one.

Binding between an anti-GPC3 antibody and GPC3 protein is generally performed in a buffer. Examples of the buffer to be employed include phosphate buffer, Tris buffer, citrate buffer, borate buffer, and carbonate buffer. Incubation is performed under generally employed conditions (e.g., 4° C. to room temperature, one hour to 24 hours). No particular limitation is imposed on the substance to be employed for washing after incubation, so long as it does not impede binding between GPC3 protein and an anti-GPC3 antibody. For example, a buffer containing a surfactant (e.g., Tween 20) is employed.

In the GPC3 protein measuring method of the present invention, a control sample may be provided in addition to a test sample containing GPC3 protein to be measured. The control sample may be, for example, a negative control containing no GPC3 protein, or a positive control sample containing GPC3 protein. In such a case, measurement of GPC3 protein contained in a test sample can be performed through comparison with the results obtained from a negative control sample containing no GPC3 protein, or the results obtained from a positive control sample containing GPC3 protein. Alternatively, quantitative measurement of GPC3 protein contained in a test sample can be performed, by use of data of the test sample, on the basis of a standard curve formed by use of data corresponding to the measurement results obtained from a series of control samples which have been prepared to have stepwise different GPC3 concentrations.

A preferred mode of the method for measurement of GPC3 protein bound to a support via an anti-GPC3 antibody is a method employing an anti-GPC3 antibody labeled with a labeling substance.

For example, a test sample is brought into contact with an anti-GPC3 antibody immobilized on a support, followed by washing, and subsequently GPC3 protein is measured by use of a labeled antibody which specifically recognizes the GPC3 protein.

Labeling of an anti-GPC3 antibody can be performed through a generally known method. Examples of the labeling substance which may be employed include labeling substances which are known to those skilled in the art, such as fluorescent dyes, enzymes, coenzymes, chemiluminescent substances, and radioactive substances. Specific examples include radioisotopes (e.g., $^{32}P$, $^{14}C$, $^{125}I$, $^{3}H$, and $^{131}I$, fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, and biotin. In the case where biotin is employed as a labeling substance, preferably, after addition of a biotin-labeled antibody, avidin bound to an enzyme (e.g., alkaline phosphatase) is further added. Binding between a labeling substance and an anti-GPC3 antibody can be performed through a known method such as the glutaraldehyde method, the maleimide method, the pyridyl disulfide method, or the periodate method.

Specifically, a solution containing an anti-GPC3 antibody is added to a support (e.g., a plate), to thereby immobilize the anti-GPC3 antibody on the support. After the plate is washed, the antibody is blocked with, for example, BSA, gelatin, or albumin, in order to prevent non-specific protein binding. After the plate is washed again, a test sample is added to the plate. After incubation, the plate is washed, and a labeled anti-GPC3 antibody is added. After appropriate incubation, the plate is washed, followed by measurement of the labeled anti-GPC3 antibody remaining on the plate. This measurement can be performed through a method known to those skilled in the art. For example, in the case where the anti-GPC3 antibody is labeled with a radioactive substance, measurement can be performed through the liquid scintillation method or the RIA method. In the case where the anti-GPC3 antibody is labeled with an enzyme, a substrate is added, and enzymatic change of the substrate (e.g., color development) is measured by means of a spectrophotometer. Specific examples of the substrate which may be employed include 2,2-azinobis(3-ethylbenzothiazoline-6-sulfonic acid) diammonium salt (ABTS), 1,2-phenylenediamine (o-phenylenediamine), and 3,3',5,5'-tetramethylbenzidine (TME). In the case where the anti-GPC3 antibody is labeled with a fluorescent substance, measurement is performed by means of a fluorometer.

A particularly preferred mode of the GPC3 protein measuring method of the present invention is a method employing a biotin-labeled anti-GPC3 antibody and avidin.

Specifically, a solution containing an anti-GPC3 antibody is added to a support (e.g., a plate), to thereby immobilize the anti-GPC3 antibody on the support. After the plate is washed, the antibody is blocked with, for example, BSA, in order to prevent non-specific protein binding. After the plate is washed again, a test sample is added to the plate. After incubation, the plate is washed, and a biotin-labeled anti-GPC3 antibody is added. After appropriate incubation, the plate is washed, and avidin bound to an enzyme (e.g., alkaline phosphatase or peroxidase) is added. After incubation, the plate is washed, and a substrate corresponding to the enzyme bound to avidin is added, followed by measurement of GPC3 protein on the basis of, for example, enzymatic change of the substrate.

Another mode of the GPC3 protein measuring method of the present invention is a method employing one or more primary antibodies which specifically recognize GPC3 protein, and one or more secondary antibodies which specifically recognize the primary antibodies.

For example, a test sample is brought into contact with one or more anti-GPC3 antibodies immobilized on a support, followed by incubation. Subsequently, the support is washed, and then GPC3 protein bound to the antibodies is measured by means of a primary anti-GPC3 antibody and one or more secondary antibodies which specifically recognize the primary antibody. In this case, preferably, the secondary antibodies are labeled with a labeling substance.

Another mode of the GPC3 protein measuring method of the present invention is a measuring method employing agglutination reaction. In this method, GPC3 measurement can be performed by use of a support sensitized with an anti-GPC3 antibody. The support to be sensitized with the antibody may be any support, so long as it is insoluble, does not cause non-specific reaction, and is stable. For example, latex particles, bentonite, collodion, kaolin, or fixed sheep erythrocyte may be employed. Preferably, latex particles are employed. Examples of the latex particles which may be employed include polystyrene latex particles, styrene-butadiene copolymer latex particles, and polyvinyl toluene latex particles. Preferably, polystyrene latex particles are employed. The thus-sensitized particles are mixed with a sample, and the resultant mixture is stirred for a predetermined period of time. The higher the level of GPC3 contained in the sample is, the greater the degree of agglutination of the particles is observed. Therefore, the GPC3 level can be measured through visual observation of the particle agglutination.

Alternatively, the GPC3 level can be determined by measuring the degree of turbidity due to the particle agglutination by means of, for example, a spectrophotometer.

Another mode of the GPC3 protein measuring method of the present invention is a method employing, for example, a biosensor utilizing surface plasmon resonance phenomenon. A biosensor utilizing surface plasmon resonance phenomenon enables real-time observation of protein-protein interaction in the form of surface plasmon resonance signal by use of a very small amount of protein without labeling. For example, binding between GPC3 protein and an anti-GPC3 antibody can be measured by means of a biosensor such as BIA core (product of Pharmacia). Specifically, a test sample is brought into contact with a sensor chip on which an anti-GPC3 antibody has been immobilized, and GPC3 protein which is bound to the anti-GPC3 antibody can be measured by change in surface plasmon resonance signal.

The measuring method of the present invention can be automated by means of a variety of automatic test systems, whereby a large number of samples can be tested at a time.

The present invention contemplates provision of a post-treatment-liver-cancer-recurrence-prognosing agent. The prognosing agent contains at least an anti-GPC3 antibody. When the prognosing agent is based on ELISA, the agent may contain a support for immobilizing the antibody, or the antibody may be bound to the support in advance. When the prognosing agent is based on the agglutination method employing a support such as latex, the agent may contain an antibody-conjugated support thereon. The prognosing agent may be provided in the form of an appropriate kit containing, for example, a blocking solution, a reaction solution, a reaction terminating solution, or reagents for treating a sample.

In order to predict recurrence of liver cancer after treatment thereof, GPC level is measured before liver cancer treatment, in an early stage after treatment (one to two weeks after treatment), or in a middle stage after treatment (two weeks to two months after treatment). The higher the level of serum GPC3 as measured in any of these stages, the higher the possibility of recurrence of liver cancer. For example, when the serum GPC3 level is 1 ng/mL or more as measured before liver cancer treatment, in an early stage after treatment, or in a middle stage after treatment, the possibility of liver cancer recurrence is predicted to be high, whereas when the serum GPC3 level is less than 1 ng/mL as measured in any of these stages, the possibility of liver cancer recurrence is predicted to be low.

EXAMPLES

The present invention will next be described in detail by way of Examples, which should not be construed as limiting the invention thereto.

Example 1

Preparation of Soluble Recombinant GPC3

By use of plasmid DNA containing full-length human GPC3 cDNA, plasmid DNA which expresses flag tagged soluble GPC3 (i.e., recombinant GPC3 cDNA) was constructed. PCR was performed by use of a downstream primer (5'-ATAGAATTCCACCATGGCCGGGACCGTGCGC-3' (SEQ ID NO: 1)) designed to eliminate a hydrophobic region (564 to 580 amino acids) on the C-terminal side, and an upstream primer (5'-ATAGGATCCCTTCAGCGGGGAAT-GAACGTTC-3' (SEQ ID NO: 2)) provided with an EcoRI recognition sequence and a Kozak sequence. The resultant PCR fragment (1,711 bp) was cloned into pCXND2-Flag.

The thus-prepared expression plasmid DNA was introduced into a CHO cell DXB11 line, followed by selection with Geneticin (500 µg/mL), to thereby yield a CHO line which highly expresses soluble GPC3.

Mass-culturing of the CHO cell line which highly expresses flag tagged soluble GPC3 was performed by means of a roller bottle of 1,700 cm$^2$, and then the resultant culture supernatant was collected and purified. The culture supernatant was applied to DEAE Sepharose Fast Flow (Amersham, CAT# 17-0709-01) and then washed, followed by elution with a buffer containing 500 mM NaCl. The subsequent purification was performed by use of Anti-Flag M2 agarose affinity gel (SIGMA, CAT# A-2220). Elution was performed with FLAG peptide (200 µg/mL). After concentration by means of Centriprep-10 (Millipore, CAT# 4304), the FLAG peptide was removed through gel filtration by means of Superdex 200 HR 10/30 (Amersham, CAT# 17-1088-01). Finally, concentration was performed by means of DEAE Sepharose Fast Flow column, and simultaneously elution was performed with phosphate buffer (containing 500 mM NaCl(containing no Tween 20) for buffer substitution, to thereby yield soluble recombinant GPC3.

Example 2

Preparation of Soluble Natural GPC3

HuH6 cell (hepatoblastoma-derived cell line), which serves as a soluble-GPC3-producing cell, was purchased from Riken Cell Bank, and was cultured in 10% FBS/Dulbecco's Modified Eagle Medium (DMEM) (SIGMA CAT# D6429)/penicillin-streptomycin (GIBCO BRL CAT#15140-122). Specifically, the HuH6 cell was mass-cultured by means of a dish with a diameter of 150 mm, and the resultant culture supernatant was collected and purified. The culture supernatant was applied to DEAE Sepharose Fast Flow (Amersham, CAT#17-0709-01) and then washed, followed by elution with a buffer containing 500 mM NaCl. Subsequently, concentration was performed by means of Centriprep-10 (Millipore, CAT#4304), followed by purification through gel filtration by means of Superdex 200 HR 10/30 (Amersham, CAT#17-1088-01), to thereby yield roughly purified natural GPC3.

Highly pure natural GPC3 was prepared as follows. An affinity column was prepared by use of an anti-mouse monoclonal antibody or an anti-guinea pig polyclonal antibody. Namely, a culture supernatant of the HuH6 cell line was applied to the affinity column and then washed with 0.1 M glycine-HCl (pH 3.5), followed by elution with 4 M MgCl$_2$.6H$_2$O and then dialysis against 50 mM Tris-HCl (pH 7.5) containing 150 mM NaCl, to thereby yield highly-pure soluble natural GPC3.

Example 3

Preparation of Anti-Soluble-GPC3 Polyclonal Antibody

A guinea pig polyclonal antibody was prepared by use of the soluble recombinant GPC3 or the soluble natural GPC3. The polyclonal antibody was prepared through a known method. Specifically, the GPC3 was emulsified with an adjuvant, and the resultant emulsion was subcutaneously administered for immunization. This immunization was repeated several times. After an increase in antibody titer was confirmed, blood was collected, and serum was obtained, followed by ammonium sulfate precipitation, to thereby yield the polyclonal antibody.

Example 4

Preparation of Anti-GPC3 Monoclonal Antibody

Five Balb/c mice (CRL) were immunized with the soluble recombinant GPC3 or the soluble natural GPC3. In the first immunization, the immunogen was prepared to attain a predetermined dose (10 μg/mouse for the case of the soluble natural GPC3, or 100 μg/mouse for the case of the soluble recombinant GPC3); the resultant preparation was emulsified with FCA (Freund's complete adjuvant (H37 Ra): Difco (3113-60) or Becton Dickinson (cat#231131)); and the resultant emulsion was subcutaneously administered. Two weeks after the first immunization, the immunogen was prepared to attain a predetermined dose (5 μg/mouse for the case of the soluble natural GPC3, or 50 μg/mouse for the case of the soluble recombinant GPC3); the resultant preparation was emulsified with FIA (Freund's incomplete adjuvant: Difco (0639-60) or Becton Dickinson (cat#263910)); and the resultant emulsion was subcutaneously administered. Thereafter, booster was performed at intervals of one week (total: five times). In the final immunization, the immunogen was diluted with PBS so as to attain a predetermined dose (5 μg/mouse for the case of the soluble natural GPC3, or 50 μg/mouse for the case of the soluble recombinant GPC3), and the resultant solution was administered via the tail vein. After saturation of anti-GPC3 antibody titer in serum was determined through ELISA employing an immunoplate coated with GPC3 core protein, mouse myeloma cell P3U1 was fused with mouse splenocyte by use of PEG1500 (Roche Diagnostic, cat#783 641). The resultant hybridoma was seeded into a 96-well culture plate, and, from the following day, selective culture was performed in HAT medium. Thereafter, the resultant culture supernatant was subjected to screening with ELISA. A positive clone was subjected to monocloning by means of limiting dilution, followed by extended culture, and the resultant culture supernatant was collected. Screening with ELISA was performed on the basis of binding activity to GPC3 core protein. Thus, an anti-GPC3 monoclonal antibody exhibiting high GPC3 binding ability was obtained.

Antibody purification was performed by means of Hi Trap ProteinG HP (Amersham cat#17-0404-01). The hybridoma culture supernatant was applied directly to the column, and then washed with a buffer (20 mM sodium phosphate (pH 7.0) for binding), followed by elution with a buffer (0.1 M glycine-HCl (pH 2.7) for elution). The resultant eluate was collected in a tube containing a buffer (1M Tris-HCl (pH 9.0) for neutralization), and neutralized immediately after collection. After antibody fractions were pooled, the antibody fractions were dialyzed against 0.05% Tween 20/PBS for one day for buffer substitution. $NaN_3$ was added to the thus-purified antibody so as to attain a concentration of 0.02%, and subsequently the antibody was stored at 4° C.

Hybridomas obtained from the soluble natural GPC3 were named "PPMX008" and "PPMX009." Hybridomas obtained from the soluble recombinant GPC3 were named "PPMX0010" and "PPMX031."

Among the thus-obtained hybridomas, PPMX009, which exhibited high sensitivity and excellent specificity in the below-described ELISA, was named "M18D04," and deposited with International Patent Organism Depositary, National Institute of Advanced Industrial Science and Technology (Central 6, 1-1-1, Higashi, Tsukuba, Ibaraki, Japan, Postal Code 305-8566; deposition date: Sep. 7, 2004; accession number: FERM ABP-10325).

Example 5

Analysis of Anti-GPC3 Monoclonal Antibody

Antibody concentration was determined through mouse IgG sandwich ELISA goat anti-mouse IgG (gamma) (ZYMED CAT# 62-6600) and alkaline phosphatase-goat anti-mouse IgG (gamma) (ZYMED CAT# 62-6622) by use, as a standard, of a commercially available purified mouse IgG1 antibody (ZYMED cat# 02-6100).

Isotyping of anti-GPC3 monoclonal antibodies was performed by employing ImmunoPure Monoclonal Antibody Isotyping Kit II (PIERCE CAT# 37502) according to the manual attached thereto. As a result of isotyping, all antibodies were IgG1 type.

Example 6

Establishment of Sandwich ELISA System

For measurement of blood GPC3, a number of sandwich ELISA systems for GPC3 measurement were established, and a measurement system in terms of excellent sensitivity and specificity was selected. The most excellent results were obtained by a system including a 96-well plate coated with PPMX042 antibody, which is a polyclonal antibody, and M18D04 antibody labeled with biotin. In order to achieve high measurement sensitivity, TMB (product of Scytek) was employed for color development.

An anti-GPC3 monoclonal or polyclonal antibody was diluted with PBS(−) so as to attain a concentration of 10 μg/mL, and a 96-well immunoplate was coated with the thus-diluted antibody, followed by incubation at 4° C. overnight. On the following day, the plate was washed three times with PBS (300 μL/well), and subsequently Immunoassay Stabilizer (product of ABI, #10-601-001) (150 μL) was added for blocking of the plate. After the plate was maintained at room temperature for several hours or at 4° C. overnight, a solution prepared by appropriately diluting purified protein, human serum, or the like with a dilution buffer (50 mM Tris-Cl pH 8.0, 0.15 M NaCl) containing animal serum, etc. was added, followed by incubation at room temperature for two hours. Subsequently, a biotin-labeled anti-GPC3 monoclonal or polyclonal antibody diluted to 20 μg/mL with PBS(−) containing animal serum, etc. was added, followed by incubation at room temperature for two hours. After the resultant reaction mixture was disposed, Streptavidin-HRPO (product of Vector, #SA-5004) diluted to 3 μg/mL with Stab-ELISA-r (product of Cygnus, #I-030) containing an appropriate amount of animal serum was added, followed by incubation at room temperature for 0.5 hours. The immunoplate was washed five times with a washing buffer (300 μL/well), followed by color development by means of TMB (product of Scytek, Cat# TM4999) according to the attached protocol, and absorbance was measured by means of a microplate reader.

Antibody biotinylation was performed by use of Sulfo-NHS-LC-Biotin (product of Pierce, CAT#21335). The level of GPC3 in a sample was analyzed by means of spreadsheet software GlaphPad PRISM (GlaphPad software Inc., ver. 3.0). A standard curve was formed by use of purified GPC3, and as a result, there was established a measurement system which exhibits low absorbance when a standard is not added, and high absorbance when GPC3 is added.

Example 7

Relation Between GPC3 Level and Recurrence in Patient who has Undergone Transcatheter Hepatic Arterial Embolization (1) Subject and Method The below-described samples were measured through the ELISA system obtained in Example 5 (i.e., a system including a 96-well plate coated with PPMX042 antibody, which is a polyclonal antibody, and M18D04 antibody labeled with biotin).

The subjects were 67 liver cancer operation cases (48 first episodes and 19 recurrent episodes) (mean age: 64.2 (range 26 to 88), male:female=55:12), who had negative margin, and exhibited neither vascular invasion nor distant metastasis in preoperative diagnosis. Factors contributing to recurrence-free survival were examined by means of a Cox proportional hazard model.

Examined factors: age, sex, etiology, tumor factors (maximum tumor size and number), pathological findings (differentiation degree, background liver, daughter nodule, and presence or absence of vascular invasion), and GPC3 level as measured before operation, in a postoperative early stage (one to two weeks after operation), or in a postoperative middle stage (two weeks to two months after operation).

Serum GPC3 level was measured through the method described above in Example 5.

(2) Results

Figure 1:
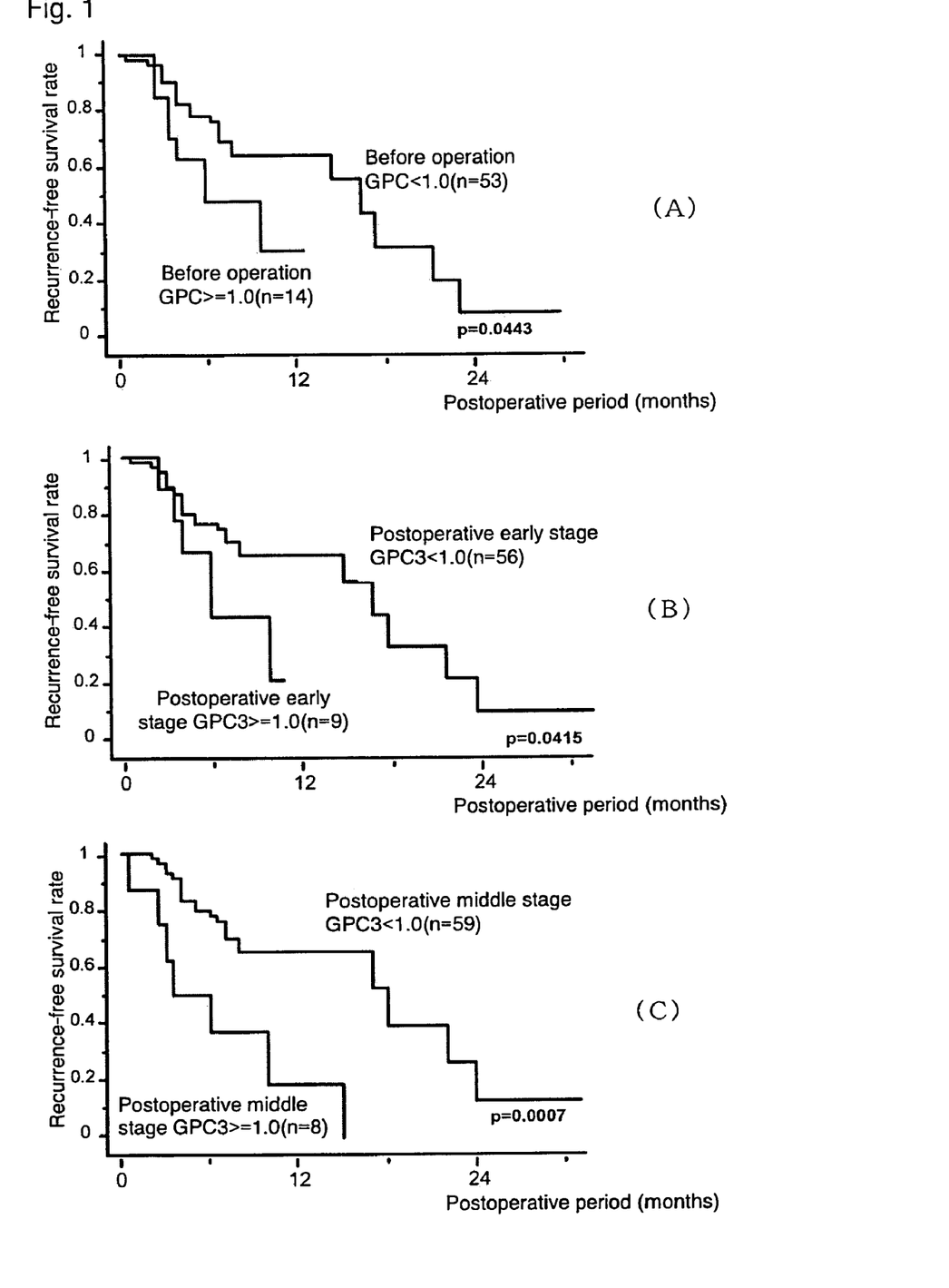
FIG. 1 Graphs showing the recurrence-free survival rate of patients whose GPC3 level is 1 ng/mL or more and that of patients whose GPC3 level is less than 1 ng/mL, the GPC3 level being measured before operation (A), one to two weeks after operation (postoperative early stage) (B), or two weeks to two months after operation (postoperative middle stage) (C). Numerical value in the lower right-hand corner of each of the graphs represents the results of Log-rank test.

There were 30 recurrent cases: lymph node recurrence (1), distant metastasis (1), recurrence at peripheral margin (1), and intrahepatic ectopic recurrence (27). Observation period was 0.5 to 32 months (mean observation period: 9.0 months). Six-month recurrence-free survival rate was found to be 73%. FIG. 1 shows the results of comparison between the recurrence-free survival rate of patients whose GPC3 level is less than 1 ng/mL and that of patients whose GPC3 level is 1 ng/mL or more, the GPC3 level being measured before operation (A), one to two weeks after operation (B), or two weeks to two months after operation (C). Statistical analysis was performed through the Log-rank test. As shown in FIG. 1, in each of the cases where the GPC3 level is measured in the preoperative stage, the postoperative early stage, and the postoperative middle stage, the recurrence-free survival rate of patients whose GPC3 level is less than 1 ng/mL is significantly higher than that of patients whose GPC3 level is 1 ng/mL or more (preoperative stage: P=0.0443, postoperative early stage: P=0.0415, and postoperative middle stage: P=0.0007, which were obtained through the Log-rank test). Thus, as is clear from the results, GPC3 level measurement is useful for prognosing postoperative recurrence, and serum GPC3 could be a useful marker for prognosing recurrence of liver cancer after treatment thereof.

Example 8

Typical Cases Showing the Relation Between Post-Transcatheter Hepatic Arterial Embolization GPC3 Level and Recurrence Table 1 shows some of the cases analyzed in Example 6, in which tumor markers other than GPC3 (i.e., AFP, PIVKA-II, and AFP-L3 fraction) were measured. In each of these cases, postoperative GPC3 level is equal to or higher than a cut-off value of 0.4. Among the tumor markers other than GPC3, AFP level is generally low, although the level is equal to or higher than a cut-off value of 20 after the second TAE in case No. 834 and in almost all the periods in case No. 287. PIVKA-II level is equal to or higher than a cut-off value of 40 after operation in case No. 975, but is low in the cases other than case No. 975. AFP-L3 fraction level is equal to or higher than a cut-off value of 15 only after the third TAE in case No. 184 and at recurrence in case No. 975. The results of these cases suggest that liver cancer recurrence can be predicted by GPC3, although such recurrence cannot be predicted by any of the tumor markers other than GPC3.

TABLE 1

| Case No. | Time course | Blood collection date | GPC3 | AFP | PIVKA-II | AFP-L3 | Age |
|---|---|---|---|---|---|---|---|
| 834 | Before operation | 2003.05.07 | 1.65 | 11 | 64 | 4.4 | 79 |
| | 4 Days after operation | 2003/05/13 | 0.23 | 5 | 29 | | |
| | 2 Weeks after operation | 2003/05/27 | 0.36 | 8 | 17 | 0 | |
| | 1 Month after operation | 2003/06/05 | 0.36 | 9 | 16 | | |
| | Cancer recurrence 3.5 months after operation, before first TAE | 2003.08.28 | 1.71 | 14 | 19 | | |
| | 1 Month after TAE treatment | 2003.10.07 | 1.07 | 10 | 20 | | |
| | 3 Months after TAE treatment, before TAE | 2003.12.02 | 4.7 | 17 | 35 | | |
| | 1 week after second TAE | 2004.01.13 | >5 | 50 | | | |
| 184 | Before operation | 2001/02/22 | 0.32 | 25 | 21 | 1.7 | 65 |
| | 7 Days after operation | 2001/03/30 | | 10 | 24 | | |
| | 4 Weeks after operation | 2001/04/19 | 0.32 | 7 | 33 | | |
| | 8 Weeks after operation | 2001/05/15 | 0.3 | 7 | 35 | | |
| | Cancer recurrence, 9 days after first TAE | 2002.07.31 | 0.27 | | | | |
| | Re-recurrence of cancers | 2002.11.26 | 0.52 | 16 | | 8.8 | |
| | Second TAE treatment | 2003/02/17 | 1.03 | 10 | 16 | | |
| | 1 Month after TAE treatment | 2003/03/13 | 0.83 | 14 | | 9.7 | |
| | 2 Months after TAE treatment | 2003/04/10 | 0.92 | 11 | | | |
| | 3 Months after TAE treatment | 2003/05/08 | 1.29 | | 19 | | |
| | Immediately before third TAE treatment | 2003/07/03 | 1.41 | 15 | | 18.6 | |

TABLE 1-continued

| Case No. | Time course | Blood collection date | GPC3 | AFP | PIVKA-II | AFP-L3 | Age |
|---|---|---|---|---|---|---|---|
|  | 1 Month after third TAE treatment | 2003.08.07 | 0.77 | 11 |  | 15 |  |
|  |  | 2003.11.06 | 3.6 |  | 18 |  |  |
|  | Before fourth TAE | 2003.12.02 | 4.2 | 16 | 15 | 38 |  |
|  | 1 Month after fourth TAE | 2004.01.22 | >5 | 17 | 18 |  |  |
| 975 | Before operation | 2001/05/23 | 0.13 | 13 | 16 | 3 | 73 |
|  | 8 Days after operation | 2001/06/19 | 0.41 | 7 | 13 |  |  |
|  | Recurrence of cancers 2 years later | 2003.09.29 | 1.16 | 12 | 72 |  |  |
|  | Before re-operation | 2003.11.04 | 2.1 | 12 | 68 | 39.6 |  |
| 287 | Before TAE treatment | 2002.07.25 | 0.59 | 18 | 10 | 10.5 | 71 |
|  | Ditto | 2002.12.12 | 0.72 |  |  |  |  |
|  | Ditto | 2003/02/06 | 0.91 | 22 | 10 | 7.8 |  |
|  | Ditto | 2003/03/06 | 0.72 | 31 | 10 | 12.6 |  |
|  | 1 Day before first TAE treatment | 2003/05/02 | 0.74 | 17 | 10 | 6.4 |  |
|  | 3 Weeks after first TAE treatment | 2003/05/22 | 0.92 | 17 | 11 | 2.1 |  |
|  | 6 Weeks after first TAE treatment | 2003.06.10 | 1.09 | 16 | 10 |  |  |
|  | 2 Weeks after second TAE | 2003.07.31 | 1.34 | 28 | 13 | 8.3 |  |
|  | 4 Months after second TAE | 2003.11.17 | 1 | 24 | 10 | 8 |  |
|  | 1 Month after third TAE | 2004.01.15 | 0.79 | 20 | 10 | 3.3 |  |
|  | Recurrence of cancers | 2004.02.09 | 1.03 | 21 | 10 | 5.1 |  |
| * | cut-off value |  | 0.4 | 20 | 40 | 15 |  |

The invention claimed is:

1. A method for prognosing the recurrence of liver cancer in a subject previously treated for liver cancer comprising:
   quantitatively determining the level of GPC3 in a biological sample of blood, plasma or serum obtained from a subject previously treated for liver cancer using an anti-GPC3 antibody or an anti-soluble GPC3 antibody, and providing a prognosis of recurrence of liver cancer in a subject previously treated for liver cancer;
   wherein a level of GPC3 of 1 ng/mL or more in the biological sample of said subject is prognostic of the recurrence of liver cancer.

2. The method of claim 1, wherein said biological sample is blood.

3. The method of claim 1, wherein the biological sample is plasma.

4. The method of claim 1, wherein the biological sample is serum.

5. The method of claim 1, wherein said subject has undergone hepatectomy, radiofrequency ablation therapy, or ethanol injection therapy.

6. The method of claim 1, wherein the antibody is an anti-soluble-GPC3 antibody.

7. The method of claim 1, wherein GPC3 in the biological sample is measured immunologically.

8. The method of claim 1, wherein the GPC3 in the biological sample is measured using ELISA.

9. The method of claim 1, further comprising a positive or negative control sample.

10. The method of claim 1, wherein GPC3 in the biological sample is measured by agglutination.

11. The method of claim 1, wherein GPC3 in the biological sample is measured by a biosensor utilizing surface plasmon resonance.

12. The method of claim 1, further comprising measuring the subject's GPC3 level prior to treatment for liver cancer.

13. The method of claim 1, comprising measuring the subject's GPC3 level one to two weeks after treatment for liver cancer.

14. The method of claim 1, comprising measuring the subject's GPC3 level two weeks to two months after treatment for liver cancer.

* * * * *

SEQUENCE LISTING

```
<160> NUMBER OF SEQ ID NOS: 2

<210> SEQ ID NO 1
<211> LENGTH: 31
<212> TYPE: DNA
<213> ORGANISM: Artificial sequence
<220> FEATURE:
<223> OTHER INFORMATION: Primer sequence for amplification of GPC3

<400> SEQUENCE: 1
atagaattcc accatggccg ggaccgtgcg c                              31

<210> SEQ ID NO 2
<211> LENGTH: 31
<212> TYPE: DNA
<213> ORGANISM: Artificial sequence
<220> FEATURE:
<223> OTHER INFORMATION: Primer sequence for amplification of GPC3

<400> SEQUENCE: 2
ataggatccc ttcagcgggg aatgaacgtt c                              31
```